US012312320B2

United States Patent
Yu et al.

(10) Patent No.: US 12,312,320 B2
(45) Date of Patent: May 27, 2025

(54) METHOD FOR SYNTHESIZING N-SUBSTITUTED PHENYL-5-HYDROXYMETHYL-2-OXAZOLIDINONE

(71) Applicant: HANGZHOU DIKE TECHNOLOGIES CO., LTD., Hangzhou (CN)

(72) Inventors: Dihu Yu, Hangzhou (CN); Quan Wang, Hangzhou (CN); Lei Bao, Hangzhou (CN); Dapeng Hou, Hangzhou (CN)

(73) Assignee: HANGZHOU DIKE TECHNOLOGIES CO., LTD., Hangzhou (CN)

( * ) Notice: Subject to any disclaimer, the term of this patent is extended or adjusted under 35 U.S.C. 154(b) by 742 days.

(21) Appl. No.: 17/636,869

(22) PCT Filed: Feb. 10, 2020

(86) PCT No.: PCT/CN2020/074576
§ 371 (c)(1),
(2) Date: Feb. 19, 2022

(87) PCT Pub. No.: WO2021/031533
PCT Pub. Date: Feb. 25, 2021

(65) Prior Publication Data
US 2022/0267284 A1 Aug. 25, 2022

(30) Foreign Application Priority Data
Aug. 20, 2019 (CN) .......................... 201910771167.0

(51) Int. Cl.
*C07D 263/24* (2006.01)
(52) U.S. Cl.
CPC ................. *C07D 263/24* (2013.01)
(58) Field of Classification Search
None
See application file for complete search history.

(56) References Cited

FOREIGN PATENT DOCUMENTS

| CN | 1772750 | 5/2006 |
|---|---|---|
| WO | WO9507271 | 3/1995 |
| WO | WO2012114355 | 2/2012 |
| WO | WO2014045292 | 3/2014 |

OTHER PUBLICATIONS

Schaus et al., J. Am. Chem. Soc., vol. 124, No. 7, pp. 1307-1315 (Year: 2002).*
Lee Yuseop et al. "Stereocontrolled, Divergent, Al(III)-Catalyzed Coupling of Chiral N-Aryl Epoxy Amines and $CO_2$", Organic Letters, vol. 20, No. 6, Aug. 6, 2018.
Osa Yumiko et al. "Convenient Synthesis of Oxazolidones by the Use of Halomethyloxirane, Primary Amine and Carbonate Salt", The Journal of Organic Chemistry, vol. 70, No. 14.

* cited by examiner

*Primary Examiner* — Zinna Northington Davis
(74) *Attorney, Agent, or Firm* — Jiwen Chen; Joywin IP Law PLLC

(57) ABSTRACT

The disclosure discloses a method for synthesizing N-substituted phenyl-5-hydroxymethyl-2-oxazolidinone, wherein the method comprises: reacting from raw materials, 3-R2-4-R1-aniline and epichlorohydrin, and allowing the resulting product to react under alkaline conditions in a $CO_2$ atmosphere to obtain N-substituted phenyl-5-hydroxymethyl-2-oxazolidinone, wherein $R_1$ is a morpholine group, a morpholin-3-one group or a piperazine group, and derivative groups thereof, and $R_2$ is halogen, hydrogen or lower alkyl. The method provided by the disclosure has such advantages as few steps, simple operation, cheap and easily available raw materials, mild reaction conditions, and high product yield, and is especially suitable for industrial production of antibiotic linezolid intermediates and antithrombotic drug rivaroxaban intermediates.

12 Claims, 2 Drawing Sheets

METHOD FOR SYNTHESIZING N-SUBSTITUTED PHENYL-5-HYDROXYMETHYL-2-OXAZOLIDINONE

This is a U.S. national stage application of PCT Application No. PCT/CN2020/074576 under 35 U.S.C. 371, filed Feb. 10, 2020 in Chinese, claiming priority to Chinese Patent Applications No. 201910771167.0, filed Aug. 20, 2019, all of which are hereby incorporated by reference.

FIELD OF TECHNOLOGY

The disclosure belongs to the field of pharmaceutical intermediate synthesis, in particular to a method for synthesizing N-substituted phenyl-5-hydroxymethyl-2-oxazolidinone.

BACKGROUND (R)—N-substituted phenyl-5-hydroxymethyl-2-oxazolidinone

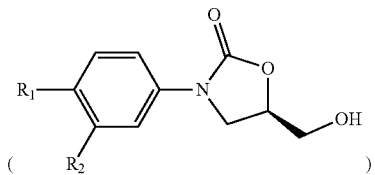

is the main structure of antibiotic linezolid intermediates

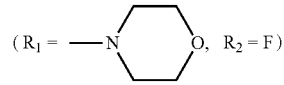

and antithrombotic drug rivaroxaban intermediates

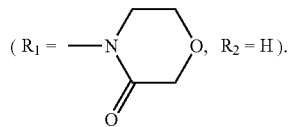

Taking linezolid intermediates as an example, they are mainly synthesized by the following methods:

The patent publication WO9507271 reports the following synthesis method:

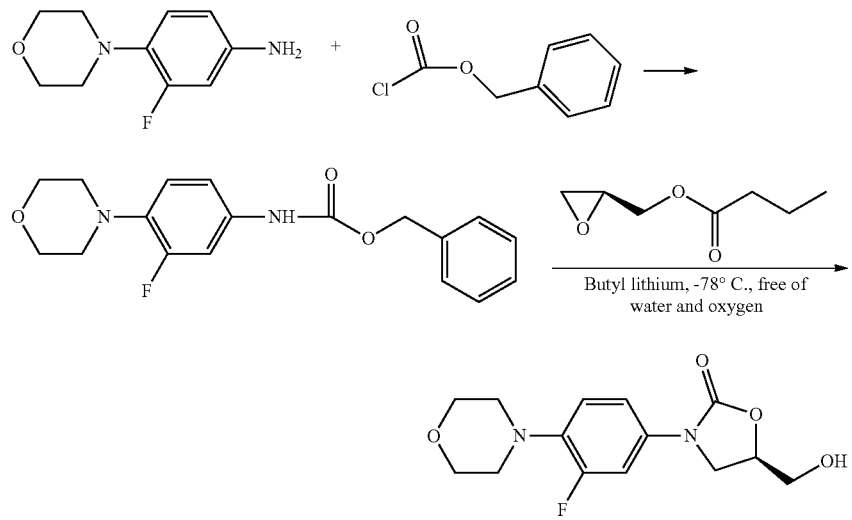

As reported in this patent, 3-fluoro-4-morpholinoaniline reacts with benzyl chloroformate, and then under the protection of nitrogen and at a temperature controlled at −78° C., the resulting product reacts with (R)-glycidyl butyrate in the presence of strong alkali n-butyl lithium to obtain the target product. This method uses highly dangerous and flammable n-butyl lithium, which requires the system to be free of water and oxygen, the reaction temperature is −78° C., so that this method is difficult to operate and dangerous, rendering it unsuitable for large-scale industrial production.

The patent publication WO2012114355 reports the following synthesis method:

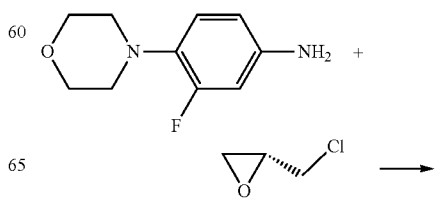

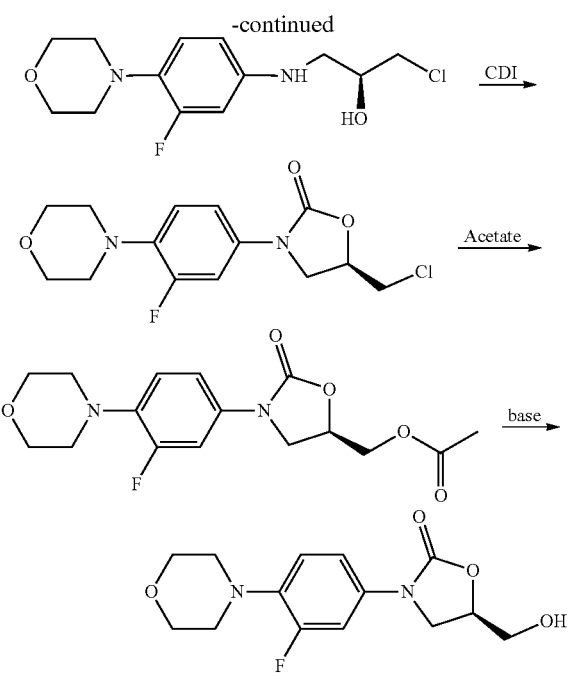

As reported in this patent, 3-fluoro-4-morpholinoaniline reacts with (R)-epichlorohydrin, the resulting product is cyclized with CDI (N,N'-carbonyldiimidazole) to obtain (5R)-3-[3-fluoro-4-(4-morpholinyl)phenyl]-5-chloromethyl-2-oxazolidinone which then reacts with sodium acetate in DMF as a solvent at 120° C., and the resulting product undergoes hydrolysis to obtain the linezolid intermediate. This process route has low yield, high impurities, many process steps and high cost.

The patent publication CN1772750 reports the following synthesis method:

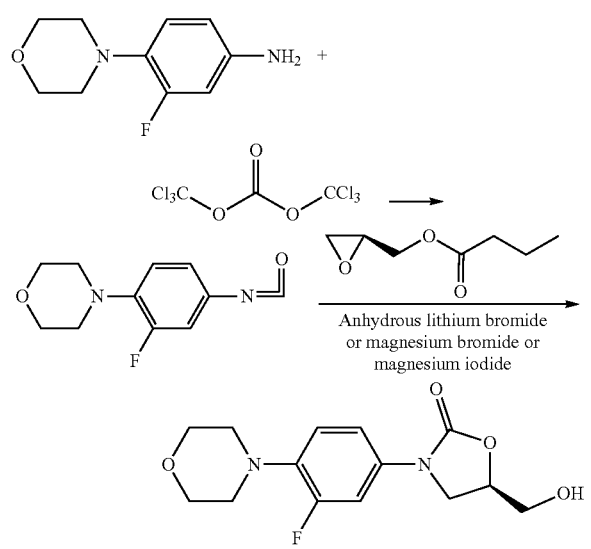

As reported in this patent, that 3-fluoro-4-morpholinoaniline reacts with triphosgene to generate (3-fluoro-4-(morpholinyl)phenyl)isocyanate, which then reacts with (R)-glycidyl butyrate to obtain the target product. Nevertheless, anhydrous lithium bromide and tributyl phosphine oxide used in this method are not readily available.

The patent publication WO2014045292A reports the following synthesis methods:

Method 1:

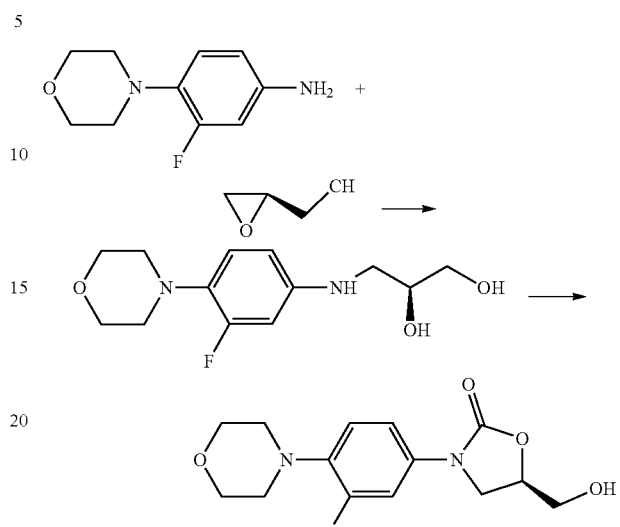

Method 2:

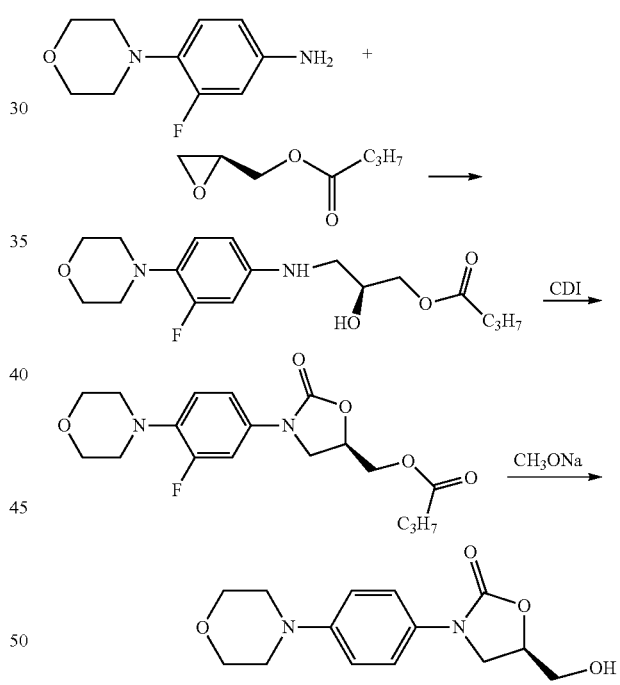

In the route of this patent, 3-fluoro-4-morpholinoaniline reacts with (R)-glycidol, then reacts with CDI or BOC anhydride, and undergoes cyclization with sodium methoxide to obtain the target product. This route has the following disadvantages: (R)-glycidol is expensive, easy to self-polymerize and generate heat, which results in potential explosion risk; 3-fluoro-4-morpholinoaniline and (R)-glycidyl butyrate are used as raw materials to react, and the reaction is incomplete, resulting in impurity dimers.

Organic letters 2018 20 (16), 5036-5039 reports a two-step method for synthesizing (R)—N-substituted phenyl-5-hydroxymethyl-2-oxazolidinone using $CO_2$ in the presence of an aluminum-based catalyst:

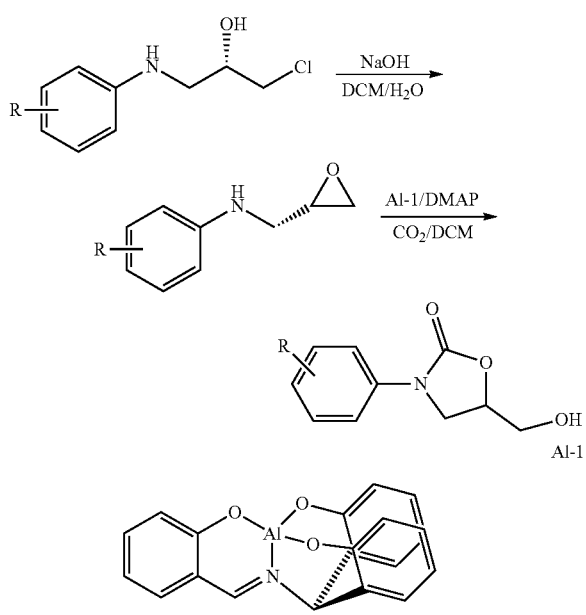

This method has simple steps, but the epoxidation of (S)-1-chloro-3-(substituted phenylamino)-2-propanol is easy to racemize, and the proportion of chiral products is reduced. In addition, an aluminum-based catalyst is used in the reaction process, and the preparation of this catalyst requires expensive raw materials and complicated process. As a result, this method is not suitable for industrial production.

Journal of Organic Chemistry, 70 (14), 5737-5740 reports the following synthesis methods:

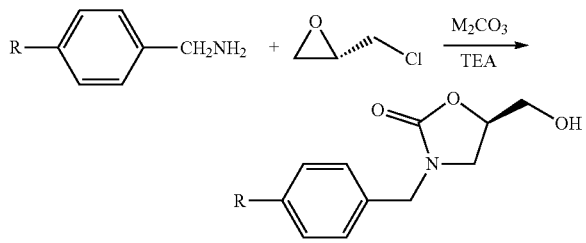

In this method, (R)—N-substituted benzyl-5-hydroxymethyl-2-oxazolidinone is prepared by the reaction of benzylamine and (S)-epichlorohydrin. Carbonates used in this reaction are sodium carbonate, potassium carbonate, rubidium carbonate, etc. In the process of reaction, the conversion rate of more than 75% can be achieved only when the carbonate and triethylamine are greatly excessive, so that the production cost of this method is high. However, this document does not report the preparation of linezolid intermediate (5R)-3-[3-fluoro-4-(4-morpholinyl)phenyl]-5-hydroxymethyl-2-oxazolidinone and rivaroxaban intermediate (R)-4-[4-(5-hydroxymethyl-2-oxooxazolidin-3-yl)-phenyl]morpholin-3-one. In addition, when this method is used to prepare the two intermediates, the yield is extremely low.

The existing methods for preparing N-substituted phenyl-5-hydroxymethyl-2-oxazolidinone are not satisfactory for industrial production.

SUMMARY OF INVENTION

An objective of the disclosure is to provide a method for synthesizing N-substituted phenyl-5-hydroxymethyl-2-oxazolidinone, which is advantageous in that it is simple, green and has high yield.

The technical solution adopted by the disclosure is as follows:

A method for synthesizing N-substituted phenyl-5-hydroxymethyl-2-oxazolidinone, wherein the method comprises: reacting from raw materials, 3-R2-4-R1-aniline and epichlorohydrin, and allowing the resulting product to react under alkaline conditions in a $CO_2$ atmosphere to obtain N-substituted phenyl-5-hydroxymethyl-2-oxazolidinone, wherein $R_1$ is a morpholine group, a morpholin-3-one group or a piperazine group, and derivative groups thereof, and $R_2$ is halogen, hydrogen or lower alkyl.

The method is a one-pot process, which comprises: preparing 1-chloro-3-(3-$R_2$-4-$R_1$-phenylamino)-2-propanol from 3-$R_2$-4-$R_1$-aniline and epichlorohydrin as raw materials, wherein $R_1$ is a morpholine group, a morpholin-3-one group or a piperazine group, and derivative groups thereof, and $R_2$ is halogen, hydrogen or lower alkyl; adding an inorganic or organic base and introducing $CO_2$ to allow 1-chloro-3-(3-$R_2$-4-$R_1$-phenylamino)-2-propanol and $CO_2$ to undergo cyclization to obtain N-substituted phenyl-5-hydroxymethyl-2-oxazolidinone.

Specifically, the reaction route of the method is as follows, wherein Formula (II) is 3-$R_2$-4-$R_1$-aniline, Formula (III) is epichlorohydrin, Formula (IV) is 1-chloro-3-(3-$R_2$-4-$R_1$-phenylamino)-2-propanol, and Formula (I) is N-substituted phenyl-5-hydroxymethyl-2-oxazolidinone:

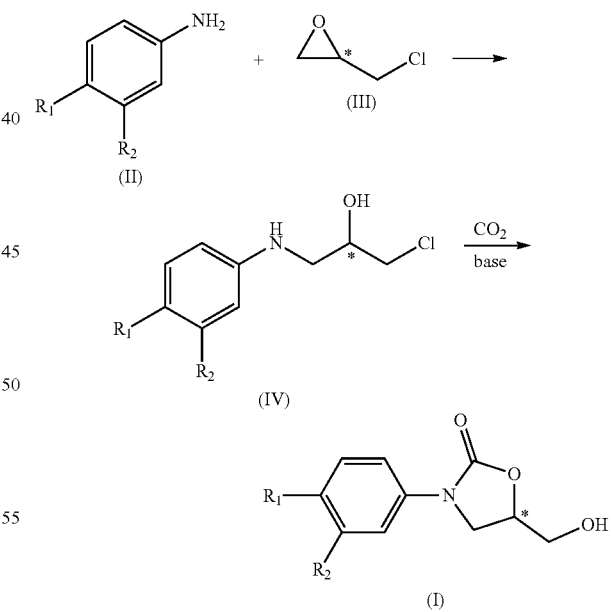

In the disclosure, with (S)-epichlorohydrin as a raw material, (R)—N-substituted phenyl-5-hydroxymethyl-2-oxazolidinone is obtained; with (R)-epichlorohydrin as a raw material, (S)—N-substituted phenyl-5-hydroxymethyl-2-oxazolidinone is obtained; and with racemic epichlorohydrin as a raw material, racemic N-substituted phenyl-5-hydroxymethyl-2-oxazolidinone is obtained.

Preferably, the 1-chloro-3-(3-$R_2$-4-$R_1$-phenylamino)-2-propanol is prepared by dissolving 3-$R_2$-4-$R_1$-aniline, epichlorohydrin and boron trifluoride diethyl ether into an organic solvent to react at 30-70° C. for 12-24 h.

Preferably, in the preparation of 1-chloro-3-(3-$R_2$-4-$R_1$-phenylamino)-2-propanol, the ratio of 3-$R_2$-4-$R_1$-aniline, epichlorohydrin and boron trifluoride diethyl ether is 0.8-5: 1:0.05-0.2.

Preferably, the cyclization is carried out at a temperature of 20-100° C.

Preferably, the molar ratio of 3-$R_2$-4-$R_1$-aniline to the inorganic or organic base is 1:1-20.

The organic base is selected from one or a combination of at least two of organic amines, sodium methoxide or sodium ethoxide.

The organic amine is selected from one or a combination of at least two of triethylamine, tetramethylguanidine, 1,8-diazabicycloundec-7-ene, pyridine, piperidine, quinoline, 4-dimethylaminopyridine or N-methylmorpholine.

The inorganic base is selected from one or a combination of at least two of sodium carbonate, potassium carbonate, trisodium phosphate or tripotassium phosphate.

Preferably, the method comprises preparing (5R)-3-[3-fluoro-4-(4-morpholinyl)phenyl]-5-hydroxymethyl-2-oxazolidinone or (R)-4-[4-(5-hydroxymethyl-2-oxooxazolidin-3-yl)-phenyl]-morpholin-3-one using 3-$R_2$-4-$R_1$-aniline and (S)-epichlorohydrin as raw materials, wherein 3-$R_2$-4-$R_1$-aniline is 3-fluoro-4-morpholinoaniline or 4-(4-aminophenyl)-morpholin-3-one.

Further preferably, the method for synthesizing (R)-4-[4-(5-hydroxymethyl-2-oxooxazolidin-3-yl)-phenyl]-morpholin-3-one is as follows: 4-(4-aminophenyl)-morpholin-3-one, (S)-epichlorohydrin and boron trifluoride diethyl ether in a molar ratio of 1:1:0.06-0.2 are dissolved in an organic solvent to react at 70° C. to obtain (S)-4-(4-((3-chloro-2-hydroxypropyl)amino)phenyl)morpholin-3-one; then pyridine or piperidine is added and $CO_2$ is introduced for cyclization at 30-50° C., thereby obtaining (R)-4-[4-(5-hydroxymethyl-2-oxooxazolidin-3-yl)-phenyl]-morpholin-3-one.

In the method provided by the disclosure, $CO_2$ plays a key role in the process of cyclization, which, compared with the method reported by Organic Letters 201820 (16), 5036-5039, avoids the cyclization process which causes racemization of the product. In addition, no catalyst is needed. As a result, the yield of chiral product of the reaction is increased and the production cost is reduced. The disclosure is beneficial in that N-substituted phenyl-5-hydroxymethyl-2-oxazolidinone can be prepared by the one-pot process using 3-$R_2$-4-$R_1$-aniline and epichlorohydrin as raw materials in a $CO_2$ atmosphere. The disclosure has such advantages as few steps, simple operation, cheap and easily available raw materials, mild reaction conditions, and high product yield, and is particularly suitable for industrial production of antibiotic linezolid intermediates and antithrombotic drug rivaroxaban intermediates.

DESCRIPTION OF THE EMBODIMENTS

Figure 1:
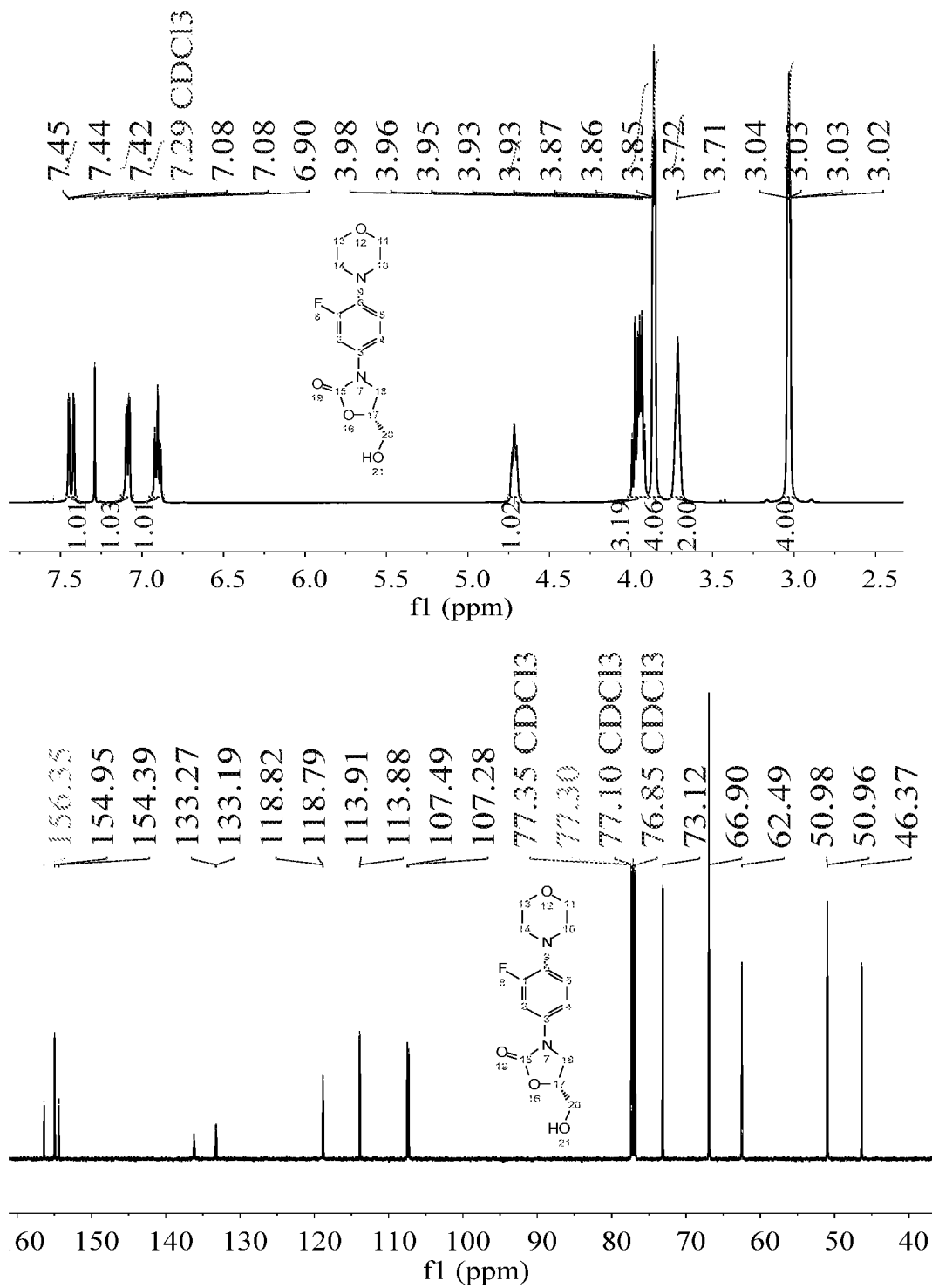
FIG. 1 is the NMR spectrum of (5R)-3-[3-fluoro-4-(4-morpholinyl)phenyl]-5-hydroxymethyl-2-oxazolidinone prepared in the examples.

In order to make the objective, technical solution and advantages of the disclosure more clear, the disclosure will be further described in detail below with reference to the drawings and examples. It should be understood that the specific embodiments described here are only for explaining the disclosure rather than limiting the scope of protection of the disclosure.

Example 1 Preparation of (5R)-3-[3-fluoro-4-(4-morpholinyl)phenyl]-5-hydroxymethyl-2-oxazolidinone 20.0 g of 3-fluoro-4-morpholinoaniline, 9.5 g of (S)-epichlorohydrin and 0.9 g of boron trifluoride diethyl ether were dissolved in 200.0 g of N,N-dimethylformamide to react at 50° C. for 16 h to prepare (S)-1-chloro-3-((3-fluoro-4-morpholinophenyl)amino)-2-propanol. Then, 32.1 g of triethylamine was added into the system which was then heated to 90° C. $CO_2$ was introduced into the solution, and after the reaction was finished, the reaction mixture was filtered and then concentrated under reduced pressure. 100 ml of water and 200 ml of dichloromethane were added, and the system was layered. The organic layer was concentrated under reduced pressure, and then 100 g of ethyl acetate was added thereto. The mixture was heated to 85° C., slowly cooled to 5° C. to crystallize, filtered and dried, thereby obtaining 22.6 g of (5R)-3-[3-fluoro-4-(4-morpholinyl)phenyl]-5-hydroxymethyl-2-oxazolidone, yield 74.8%, ee>99% as analyzed by chiral HPLC.

The NMR data of (5R)-3-[3-fluoro-4-(4-morpholinyl)phenyl]-5-hydroxymethyl-2-oxazolidinone prepared in this example: $^1$H NMR (500 MHz, Chloroform-d) δ 7.43 (dd, 1H), 7.09 (dd, 1H), 6.90 (t, 1H), 4.72 (ddt, 1H), 4.02-3.90 (m, 3H), 3.89-3.83 (m, 4H), 3.72 (q, 2H), 3.03 (dd, 4H); $^{13}$C NMR (126 MHz, CDC13) δ 156.35, 154.95, 154.39, 136.21, 133.27, 133.19, 118.82, 118.79, 113.91, 113.88, 107.49, 107.28, 77.35, 77.30, 77.10, 76.85, 73.12, 66.90, 62.49, 62.44, 50.98, 50.96, 46.37.

Example 2 Preparation of (5R)-3-[3-fluoro-4-(4-morpholinyl)phenyl]-5-hydroxymethyl-2-oxazolidinone 20.0 g of 3-fluoro-4-morpholinoaniline, 9.5 g of (S)-epichlorohydrin and 1.2 g of boron trifluoride diethyl ether were dissolved in 200.0 g of N,N-dimethylformamide to react at 40° C. for 24 h to prepare (S)-1-chloro-3-((3-fluoro-4-morpholinophenyl)amino)-2-propanol. Then, 20.0 g of a 28% sodium methoxide solution in methanol was added to the system which was then heated to 95° C. $CO_2$ was introduced into the solution, and after the reaction was finished, the reaction mixture was filtered and then concentrated under reduced pressure. 100 ml of water and 200 ml of dichloromethane were added, and the system was layered. The organic layer was concentrated under reduced pressure, and then 100 g of ethyl acetate was added thereto. The mixture was heated to 85° C., slowly cooled to 5° C. to crystallize, filtered and dried, thereby obtaining 21.8 g of (5R)-3-[3-fluoro-4-(4-morpholinyl)phenyl]-5-hydroxymethyl-2-oxazolidinone, yield 72.2%, ee>99% as analyzed by chiral HPLC.

Example 3 Preparation of (5R)-3-[3-fluoro-4-(4-morpholinyl)phenyl]-5-hydroxymethyl-2-oxazolidinone 20.0 g of 3-fluoro-4-morpholinoaniline, 9.5 g of (S)-epichlorohydrin and 0.4 g of boron trifluoride diethyl ether were dissolved in 200.0 g of N,N-dimethylformamide to react at 60° C. for 12 h to prepare (S)-1-chloro-3-((3-fluoro-4-morpholinophenyl)amino)-2-propanol. Then, 33.5 g of trisodium phosphate was added into the system which was then heated to 90° C. $CO_2$ was introduced into the solution, and after the reaction was finished, the reaction mixture was filtered and then concentrated under reduced pressure. 100 ml of water and 200 ml of dichloromethane were added, and the system was layered. The organic layer was concentrated under reduced pressure, and then 100 g of ethyl acetate was added thereto. The mixture was heated to 85° C., slowly cooled to 5° C. to crystallize, filtered and dried, thereby obtaining 22.3 g of (5R)-3-[3-fluoro-4-(4-morpholinyl)phenyl]-5-hydroxymethyl-2-oxazolidinone, yield 73.8%, ee>99% as analyzed by chiral HPLC.

Example 4 Preparation of (5R)-3-[3-fluoro-4-(4-morpholinyl)phenyl]-5-hydroxymethyl-2-oxazolidinone 20.0 g of 3-fluoro-4-morpholinoaniline, 9.5 g of (S)-epichlorohydrin and 0.9 g of boron trifluoride diethyl ether were dissolved in 200.0 g of N,N-dimethylformamide to react at 60° C. for 16 h to prepare (S)-1-chloro-3-((3-fluoro-4-morpholinophenyl)amino)-2-propanol. Then, 12.9 g of tetramethylguanidine was added into the system which was then heated to 55° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 85° C., slowly cooled to 5° C. to crystallize, filtered and dried, thereby obtaining 22.7 g of (5R)-3-[3-fluoro-4-(4-morpholinyl)phenyl]-5-hydroxymethyl-2-oxazolidinone, yield 75.2%, ee>99% as analyzed by chiral HPLC.

Example 5 Preparation of (5R)-3-[3-fluoro-4-(4-morpholinyl)phenyl]-5-hydroxymethyl-2-oxazolidinone 20.0 g of 3-fluoro-4-morpholinoaniline, 9.5 g of (S)-epichlorohydrin and 0.9 g of boron trifluoride diethyl ether were dissolved in 200.0 g of N,N-dimethylformamide to react at 60° C. for 16 h to prepare (S)-1-chloro-3-((3-fluoro-4-morpholinophenyl)amino)-2-propanol. Then, 17.0 g of DBU was added into the system which was then heated to 55° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 85° C., slowly cooled to 5° C. to crystallize, filtered and dried, thereby obtaining 22.3 g of (5R)-3-[3-fluoro-4-(4-morpholinyl)phenyl]-5-hydroxymethyl-2-oxazolidinone, yield 73.8%, ee>99% as analyzed by chiral HPLC.

Example 6 Preparation of (5R)-3-[3-fluoro-4-(4-morpholinyl)phenyl]-5-hydroxymethyl-2-oxazolidinone 20.0 g of 3-fluoro-4-morpholinoaniline, 9.5 g of (S)-epichlorohydrin and 0.9 g of boron trifluoride diethyl ether were dissolved in 200.0 g of N,N-dimethylformamide to react at 50° C. for 18 h to prepare (S)-1-chloro-3-((3-fluoro-4-morpholinophenyl)amino)-2-propanol. Then, 15.4 g of quinoline was added into the system which was then heated to 70° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 85° C., slowly cooled to 5° C. to crystallize, filtered and dried, thereby obtaining 22.1 g of (5R)-3-[3-fluoro-4-(4-morpholinyl)phenyl]-5-hydroxymethyl-2-oxazolidinone, yield 72.9%, ee>99% as analyzed by chiral HPLC.

Example 7 Preparation of (R)-4-[4-(5-hydroxymethyl-2-oxooxazolidin-3-yl)-phenyl]-morpholin-3-one 20.0 g of 4-(4-aminophenyl)-morpholin-3-one, 9.7 g of (S)-epichlorohydrin and 0.9 g of boron trifluoride diethyl ether were dissolved in 200.0 g of N,N-dimethylformamide to react at 60° C. for 14 h to prepare (S)-4-(4-((3-chloro-2-hydroxypropyl)amino)phenyl)morpholin-3-one. Then, 45 g of potassium carbonate was added into the system which was then heated to 90° C. $CO_2$ was introduced into the solution, and after the reaction was finished, the reaction mixture was filtered and then concentrated under reduced pressure. 100 ml of water and 200 ml of dichloromethane were added, and the system was layered. The organic layer was concentrated under reduced pressure, and then 100 g of ethyl acetate was added thereto. The mixture was heated to 80° C., slowly cooled to 5° C. to crystallize, filtered and dried, thereby obtaining 21.8 g of (R)-4-[4-(5-hydroxymethyl-2-oxooxazolidin-3-yl)-phenyl]-morpholin-3-one, yield 71.7%, ee>99% as analyzed by chiral HPLC.

The NMR data of (R)-4-[4-(5-hydroxymethyl-2-oxooxazolidin-3-yl)-phenyl]-morpholin-3-one prepared in this example: $^1$H NMR (500 MHz, DMSO-d6) δ 7.63-7.56 (m, 2H), 7.44-7.37 (m, 2H), 5.23 (t, 1H), 4.70 (ddt, 1H), 4.20 (s, 2H), 4.09 (t, 1H), 4.00-3.94 (m, 2H), 3.84 (dd, 1H), 3.68 (td, 2H), 3.57 (ddd, 1H); $^{13}$C NMR (126 MHz, DMSO) δ 165.94, 154.45, 136.80, 136.66, 125.92, 117.99, 73.14, 67.69, 63.45, 61.62, 48.99, 46.00, 40.05, 39.96, 39.88, 39.79, 39.71, 39.62, 39.55, 39.46, 39.38, 39.29, 39.12, 38.96.

Example 8 Preparation of (R)-4-[4-(5-hydroxymethyl-2-oxooxazolidin-3-yl)-phenyl]-morpholin-3-one 20.0 g of 4-(4-aminophenyl)-morpholin-3-one, 9.7 g of (S)-epichlorohydrin and 0.9 g of boron trifluoride diethyl ether were dissolved in 200.0 g of N,N-dimethylformamide to react at 50° C. for 16 h to prepare (S)-4-(4-((3-chloro-2-hydroxypropyl)amino)phenyl)morpholin-3-one. Then, 13.1 g of tetramethylguanidine was added into the system which was then heated to 20° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 80° C., slowly cooled to 5° C. to crystallize, filtered and dried, thereby obtaining 22.3 g of (R)-4-[4-(5-hydroxymethyl-2-oxooxazolidin-3-yl)-phenyl]-morpholin-3-one, yield 73.3%, ee>99% as analyzed by chiral HPLC.

Example 9 Preparation of (R)-4-[4-(5-hydroxymethyl-2-oxooxazolidin-3-yl)-phenyl]-morpholin-3-one 20.0 g of 4-(4-aminophenyl)-morpholin-3-one, 9.7 g of (S)-epichlorohydrin and 0.9 g of boron trifluoride diethyl ether were dissolved in 200.0 g of N,N-dimethylformamide to react at 70° C. for 13 h to prepare (S)-4-(4-((3-chloro-2-hydroxypropyl)amino)phenyl)morpholin-3-one. Then, 27.1 g of pyridine was added into the system which was then heated to 30° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 80° C., slowly cooled to 5° C. to crystallize, filtered and dried, thereby obtaining 25.3 g of (R)-4-[4-(5-hydroxymethyl-2-oxooxazolidin-3-yl)-phenyl]-morpholin-3-one, yield 83.2%, ee>99% as analyzed by chiral HPLC.

Example 10 Preparation of (R)-4-[4-(5-hydroxymethyl-2-oxooxazolidin-3-yl)-phenyl]-morpholin-3-one 20.0 g of 4-(4-aminophenyl)-morpholin-3-one, 9.3 g of (S)-epichlorohydrin and 2.8 g of boron trifluoride diethyl ether were dissolved in 200.0 g of N,N-dimethylformamide to react at 70° C. for 13 h to prepare (S)-4-(4-((3-chloro-2-hydroxypropyl)amino)phenyl)morpholin-3-one. Then, 43.0 g of piperidine was into the system which was then heated to 50° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 80° C., slowly cooled to 5° C. to crystallize, filtered and dried, thereby obtaining 26.9 g of (R)-4-[4-(5-hydroxymethyl-2-oxooxazolidin-3-yl)-phenyl]-morpholin-3-one, yield 88.4%, ee>99% as analyzed by chiral HPLC.

Example 11 Preparation of (R)-4-[4-(5-hydroxymethyl-2-oxooxazolidin-3-yl)-phenyl]-morpholin-3-one 20.0 g of 4-(4-aminophenyl)-morpholin-3-one, 9.7 g of (S)-epichlorohydrin and 0.9 g of boron trifluoride diethyl ether were dissolved in 200.0 g of N,N-dimethylformamide to react at 60° C. for 14 h to prepare (S)-4-(4-((3-chloro-2-hydroxypropyl)amino)phenyl)morpholin-3-one. Then, 17.3 g of DMAP was added into the system which was then heated to 30° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 80° C., slowly cooled to 5° C. to crystallize, filtered and dried, thereby obtaining 20.9 g of (R)-4-[4-(5-hydroxymethyl-2-oxooxazolidin-3-yl)-phenyl]-morpholin-3-one, yield 68.9%, ee>99% as analyzed by chiral HPLC.

Example 12 Preparation of (R)-4-[4-(5-hydroxymethyl-2-oxooxazolidin-3-yl)-phenyl]-morpholin-3-one 20.0 g of 4-(4-aminophenyl)-morpholin-3-one, 9.7 g of (S)-epichlorohydrin and 0.9 g of boron trifluoride diethyl ether were dissolved in 200.0 g of N,N-dimethylformamide to react at 30° C. for 24 h to prepare (S)-4-(4-((3-chloro-2-hydroxypropyl)amino)phenyl)morpholin-3-one. Then, 26.8 g of N-methylmorpholine was added into the system which was then heated to 50° C. $CO_2$ was introduced into the solution, and after the reaction was finished, the reaction mixture was concentrated under reduced pressure. 100 ml of water and 200 ml of dichloromethane were added, and the system was layered. The organic layer was concentrated under reduced pressure, and then 100 g of ethyl acetate was added thereto. The mixture was heated to 80° C., slowly cooled to 5° C. to crystallize, filtered and dried, thereby obtaining 21.9 g of (R)-4-[4-(5-hydroxymethyl-2-oxooxazolidin-3-yl)-phenyl]-morpholin-3-one, yield 72.2%, ee>99% as analyzed by chiral HPLC.

Figure 2:
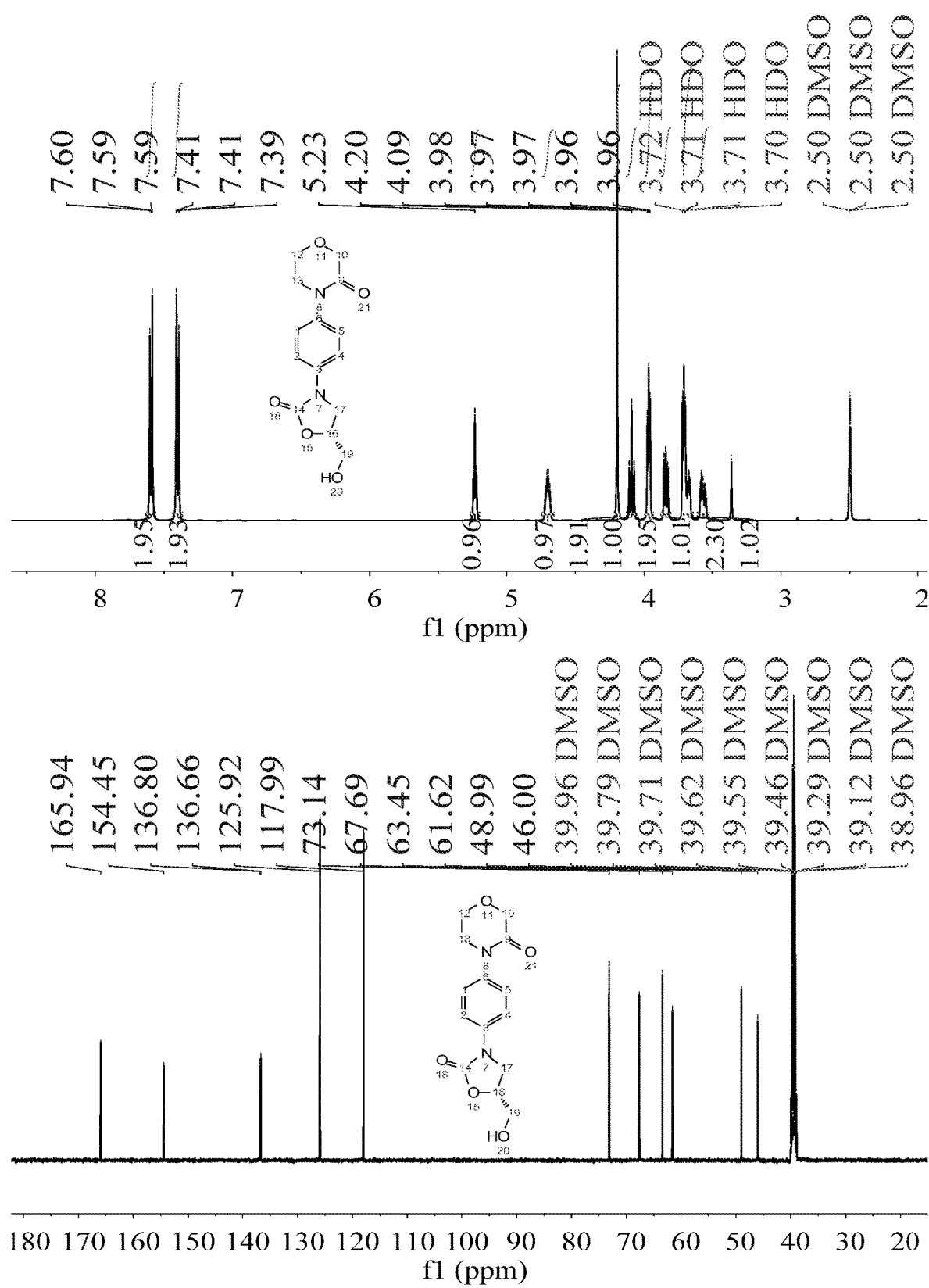
FIG. 2 is the NMR spectrum of (R)-4-[4-(5-hydroxymethyl-2-oxooxazolidin-3-yl)-phenyl]-morpholin-3-one prepared in the examples.

Among others, the NMR spectrum of (5R)-3-[3-fluoro-4-(4-morpholinyl)phenyl]-5-hydroxymethyl-2-oxazolidinone prepared in Examples 1-6 is as shown in FIG. 1, and the NMR spectrum of (R)-4-[4-(5-hydroxymethyl-2-oxooxazolidin-3-yl)-phenyl]-morpholin-3-one prepared in Examples 7-12 is as shown in FIG. 2.

The specific embodiments described above have described the technical solution and beneficial effects of the disclosure in detail. It should be understood that the above-described embodiments are only the most preferred embodiments of the disclosure, and are not used to limit the disclosure. Any modifications, supplements and equivalent replacements within the principle and scope of the disclosure should be included in the protection scope of the disclosure.

What is claimed is:

1. A method for synthesizing N-substituted phenyl-5-hydroxymethyl-2-oxazolidinone, wherein the method comprises: reacting from raw materials, 3-$R_2$-4-$R_1$-aniline and epichlorohydrin, and allowing the resulting product to react under alkaline conditions in a $CO_2$ atmosphere to obtain N-substituted phenyl-5-hydroxymethyl-2-oxazolidinone, wherein $R_1$ is a morpholine group, a morpholin-3-one group or a piperazine group, and derivative groups thereof, and $R_2$ is halogen, hydrogen or lower alkyl.

2. The method for synthesizing N-substituted phenyl-5-hydroxymethyl-2-oxazolidinone according to claim 1, wherein the method is a one-pot process comprising: preparing 1-chloro-3-(3-$R_2$-4-$R_1$-phenylamino)-2-propanol from 3-$R_2$-4-$R_1$-aniline and epichlorohydrin as raw materials, wherein $R_1$ is a morpholine group, a morpholin-3-one group or a piperazine group, and derivative groups thereof, and $R_2$ is halogen, hydrogen or lower alkyl; adding an inorganic or organic base and introducing $CO_2$ to allow 1-chloro-3-(3-$R_2$-4-$R_1$-phenylamino)-2-propanol and $CO_2$ to undergo cyclization to obtain N-substituted phenyl-5-hydroxymethyl-2-oxazolidinone.

3. The method for synthesizing N-substituted phenyl-5-hydroxymethyl-2-oxazolidinone according to claim 1, wherein with (S)-epichlorohydrin as a raw material, (R)—N-substituted phenyl-5-hydroxymethyl-2-oxazolidinone is obtained; with (R)-epichlorohydrin as a raw material, (S)—

N-substituted phenyl-5-hydroxymethyl-2-oxazolidinone is obtained; and with racemic epichlorohydrin as a raw material, racemic N-substituted phenyl-5-hydroxymethyl-2-oxazolidinone is obtained.

4. The method for synthesizing N-substituted phenyl-5-hydroxymethyl-2-oxazolidinone according to claim 2, wherein the 1-chloro-3-(3-$R_2$-4-$R_1$-phenylamino)-2-propanol is prepared by dissolving 3-$R_2$-4-$R_1$-aniline, epichlorohydrin and boron trifluoride diethyl ether into an organic solvent to react at 30-70° C. for 12-24 h.

5. The method for synthesizing N-substituted phenyl-5-hydroxymethyl-2-oxazolidinone according to claim 4, wherein the molar ratio of 3-$R_2$-4-$R_1$-aniline, epichlorohydrin and boron trifluoride diethyl ether is 0.8-5:1:0.05-0.2.

6. The method for synthesizing N-substituted phenyl-5-hydroxymethyl-2-oxazolidinone according to claim 2, wherein the cyclization is carried out at a temperature of 20-100° C.

7. The method for synthesizing N-substituted phenyl-5-hydroxymethyl-2-oxazolidinone according to claim 2, wherein the molar ratio of 3-$R_2$-4-$R_1$-aniline to the inorganic or organic base is 1:1-20.

8. The method for synthesizing N-substituted phenyl-5-hydroxymethyl-2-oxazolidinone according to claim 7, wherein the organic base is selected from one or a combination of at least two of organic amines, sodium methoxide or sodium ethoxide.

9. The method for synthesizing N-substituted phenyl-5-hydroxymethyl-2-oxazolidinone according to claim 8, wherein the organic amine is one or a combination of at least two of triethylamine, tetramethylguanidine, 1,8-diazabicycloundec-7-ene, pyridine, piperidine, quinoline, 4-dimethylaminopyridine or N-methylmorpholine.

10. The method for synthesizing N-substituted phenyl-5-hydroxymethyl-2-oxazolidinone according to claim 7, wherein the inorganic base is selected from one or a combination of at least two of sodium carbonate, potassium carbonate, trisodium phosphate or tripotassium phosphate.

11. The method for synthesizing N-substituted phenyl-5-hydroxymethyl-2-oxazolidinone according to claim 1, wherein the method comprises preparing (5R)-3-[3-fluoro-4-(4-morpholinyl)phenyl]-5-hydroxymethyl-2-oxazolidinone or (R)-4-[4-(5-hydroxymethyl-2-oxooxazolidin-3-yl)-phenyl]-morpholin-3-one using 3-$R_2$-4-$R_1$-aniline and (S)-epichlorohydrin as raw materials, wherein 3-$R_2$-4-$R_1$-aniline is 3-fluoro-4-morpholinoaniline or 4-(4-aminophenyl)-morpholin-3-one.

12. The method for synthesizing N-substituted phenyl-5-hydroxymethyl-2-oxazolidinone according to claim 2, wherein with (S)-epichlorohydrin as a raw material, (R)—N-substituted phenyl-5-hydroxymethyl-2-oxazolidinone is obtained; with (R)-epichlorohydrin as a raw material, (S)—N-substituted phenyl-5-hydroxymethyl-2-oxazolidinone is obtained; and with racemic epichlorohydrin as a raw material, racemic N-substituted phenyl-5-hydroxymethyl-2-oxazolidinone is obtained.

* * * * *